United States Patent [19]

Patel

[11] Patent Number: 5,348,947
[45] Date of Patent: Sep. 20, 1994

[54] DIARYLBORON ESTER AND THIOESTER FUNGICIDAL AGENTS

[75] Inventor: Bomi P. Patel, Philadelphia, Pa.

[73] Assignee: American Cyanamid Company, Wayne, N.J.

[21] Appl. No.: 59,155

[22] Filed: May 7, 1993

[51] Int. Cl.$^5$ .................................... A01N 55/08
[52] U.S. Cl. .................................... 514/64
[58] Field of Search .................................... 514/64

[56] References Cited

PUBLICATIONS

N. Farfan, et al., J. Chem. Soc. Perkin Trans., (2), pp. 527–532 (1992).
H. K. Zimmerman, Texas J. Sci., 15(2), pp. 192–199 (1963).
Z. Shan, et al., Wuhan Daxue Xuebao, Ziran Kexueban, (3), pp. 67–72 (1990).
K. Lin, et al, Yiyao Gongye, 16(11), pp. 500–502 (1985).
E. Hohaus and F. Umland, Chem. Ber., 102(12), pp. 4025–4031 (1969).
D. Thierig and F. Umland, Z. Anal. Chem., 215(1), pp. 24–30 (1966).
R. Neu, Arch. Pharm., 294, pp. 173–178 (1961).

Primary Examiner—Gary E. Hollinden
Assistant Examiner—Mary C. Cebulak
Attorney, Agent, or Firm—John W. Hogan, Jr.

[57] ABSTRACT

There are provided fungicidal diarylboron esters and thioesters having the structural formula

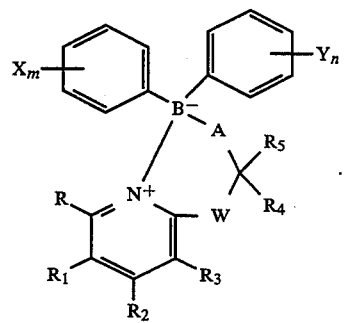

Further provided are compositions and methods for the protection of plants from fungal infestation and disease.

7 Claims, No Drawings

DIARYLBORON ESTER AND THIOESTER FUNGICIDAL AGENTS

BACKGROUND OF THE INVENTION

Phytopathogenic fungi are the causal agents for many diseases that infect and destroy crops. In particular, the diseases apple scab, tomato early blight and grape and pepper botrytis are especially devastating.

In spite of the commercial fungicides available today, diseases caused by fungi still abound. Accordingly, there is ongoing research to create new and more effective fungicides for controlling or preventing diseases caused by phytopathogenic fungi.

SUMMARY OF THE INVENTION

The present invention describes fungicidal diarylboron ester and thioester compounds.

The fungicidal diarylboron ester and thio-ester compounds useful in the methods and compositions of the present invention have the structural formula:

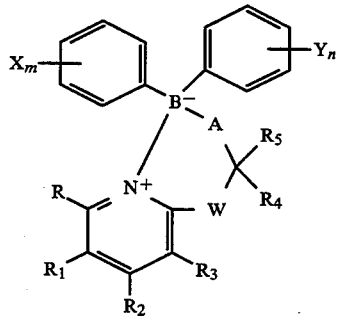

(I)

wherein
- X and Y are each independently hydrogen, halogen, $C_1$-$C_6$ alkoxy, $C_1$-$C_6$ haloalkoxy, $C_1$-$C_6$ alkyl or $C_1$-$C_6$ haloalkyl;
- m and n are each independently an integer of 0, 1, 2 or 3;
- A is O or S;
- R, $R_1$, $R_2$ and $R_3$ are each independently hydrogen, halogen, $C_1$-$C_4$ alkoxy, $C_1$-$C_4$ haloalkoxy, $C_1$-$C_4$ alkyl, $C_1$-$C_4$ haloalkyl, $C_1$-$C_4$ hydroxy alkyl, cyano, nitro, $CH_2CN$, hydroxy, $NR_6R_7$, $SO_3R_8$ or $COR_9$, and when taken together, R and $R_1$, $R_1$ and $R_2$ or $R_2$ and $R_3$ may form a ring in which $RR_1$, $R_1R_2$ or $R_2R_3$ is represented by the structure: —CH=CH—CH=CH— or —(CH$_2$)$_4$—;
- $R_4$ is hydrogen, halogen, $C_1$-$C_8$ alkoxy or $C_1$-$C_8$ alkyl;
- $R_5$ is hydrogen, halogen, $C_1$-$C_8$ alkoxy, $C_1$-$C_8$ alkyl, $NR_6R_7$, $SO_3R_8$, hydroxy, oxo or phenyl optionally substituted with one or more halogen, $C_1$-$C_4$ alkyl, $C_1$-$C_4$ haloalkyl, $C_1$-$C_4$ alkoxy or $C_1$-$C_4$ haloalkoxy groups, provided that when $R_5$ is oxo, $R_4$ is not present;
- W is (CH$_2$)$_p$;
- p is an integer of 0 or 1;
- $R_6$, $R_7$ and $R_8$ are each independently hydrogen or $C_1$-$C_4$ alkyl; and
- $R_9$ is $C_1$-$C_4$ alkyl.

This invention relates to compositions and methods for the prevention, control or amelioration diseases caused by phytopathogenic fungi.

DETAILED DESCRIPTION OF THE INVENTION

Phytopathogenic fungi are the causal agents for many diseases that infect and destroy agronomic crops, both growing and harvested. In the United States alone, agronomic crops must compete with about 18,000 species of fungi. Especially devasting are diseases such as apple scab, tomato early blight, grape or pepper botrytis and the like. Accordingly, there is ongoing research to create new and more effective fungicides for preventing or controlling the vast array of fungal infestations of crops.

Advantageously, the present invention provides a method for the prevention, control or amelioration of a disease caused by a phytopathogenic fungus by contacting said fungus with a fungicidally effective amount of a formula I, diarylboron ester or thioester compound.

The present invention also provides a method for the protection of a plant, plant seed or tuber from fungal infestation and disease by applying to the plant, plant seed or tuber, or to the medium or water in which it is growing, a fungicidally effective amount of a formula I, diarylboron ester or thioester compound.

The fungicidal diarylboron ester and thio-ester compounds of the present invention have the following structural formula I:

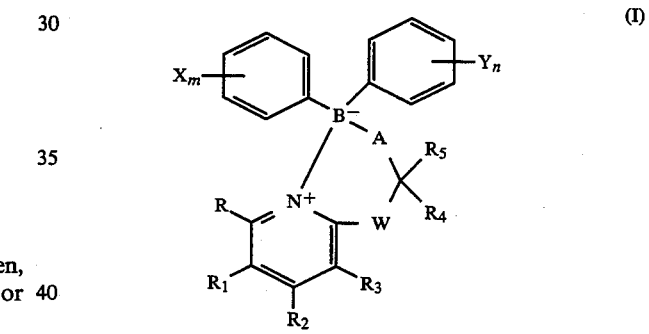

(I)

wherein
- X and Y are each independently hydrogen, halogen, $C_1$-$C_6$ alkoxy, $C_1$-$C_6$ haloalkoxy, $C_1$-$C_6$ alkyl or $C_1$-$C_6$ haloalkyl;
- m and n are each independently an integer of 0, 1, 2 or 3;
- A is O or S;
- R, $R_1$, $R_2$ and $R_3$ are each independently hydrogen, halogen, $C_1$-$C_4$ alkoxy, $C_1$-$C_4$ haloalkoxy, $C_1$-$C_4$ alkyl, $C_1$-$C_4$ haloalkyl, $C_1$-$C_4$ hydroxy-alkyl, cyano, nitro, $CH_2CN$, hydroxy, $NR_6R_7$, $SO_3R_8$ or $COR_9$, and when taken together, R and $R_1$, $R_1$ and $R_2$ or $R_2$ and $R_3$ may form a ring in which $RR_1$, $R_1R_2$ or $R_2R_3$ is represented by the structure: —CH=CH—CH=CH— or —(CH$_2$)$_4$—;
- $R_4$ is hydrogen, halogen, $C_1$-$C_8$ alkoxy or $C_1$-$C_8$ alkyl;
- $R_5$ is hydrogen, halogen, $C_1$-$C_8$ alkoxy, $C_1$-$C_8$ alkyl, $NR_6R_7$, $SO_3R_8$, hydroxy, oxo or phenyl optionally substituted with one or more halogen, $C_1$-$C_4$ alkyl, $C_1$-$C_4$ haloalkyl, $C_1$-$C_4$ alkoxy or $C_1$-$C_4$ haloalkoxy groups, provided that when $R_5$ is oxo, $R_4$ is not present;
- W is (CH$_2$)$_p$;
- p is an integer of 0 or 1;
- $R_6$, $R_7$ and $R_8$ are each independently hydrogen or $C_1$-$C_4$ alkyl; and $R_9$ is $C_1$-$C_4$ alkyl.

Preferred fungicidal agents of the present invention are diarylboron ester compounds of formula I wherein
X and Y are each independently hydrogen, halogen, $C_1$-$C_6$ alkoxy, $C_1$-$C_6$ haloalkoxy, $C_1$-$C_6$ alkyl or $C_1$-$C_6$ haloalkyl;
m and n are each independently an integer of 0, 1, 2 or 3;
A is O;
R, $R_1$, $R_2$ and $R_3$ are each independently hydrogen, halogen, $C_1$-$C_4$ alkoxy, $C_1$-$C_4$ haloalkoxy, $C_1$-$C_4$ alkyl, $C_1$-$C_4$ haloalkyl, $C_1$-$C_4$ hydroxy-alkyl, nitro, $CH_2CN$, hydroxy, $NR_6R_7$ or $SO_3R_8$, and when taken together, R and $R_1$, $R_1$ and $R_2$ or $R_2$ and $R_3$ may form a ring in which $RR_1$, $R_1R_2$ or $R_2R_3$ is represented by the structure: —CH=CH—CH=CH—;
$R_4$ is hydrogen;
$R_5$ is hydrogen, halogen, $C_1$-$C_8$ alkoxy, $C_1$-$C_8$ alkyl, $NR_6R_7$, $SO_3R_8$, hydroxy, oxo or phenyl optionally substituted with one or more halogen, $C_1$-$C_4$ alkyl, $C_1$-$C_4$ haloalkyl, $C_1$-$C_4$ alkoxy $C_1$-$C_4$ haloalkoxy groups, provided that when $R_5$ is oxo, $R_4$ is not present;
W is $(CH_2)_p$;
p is an integer of 0 or 1; and
$R_6$, $R_7$ and $R_8$ are each independently hydrogen or $C_1$-$C_4$ alkyl.

More preferred formula I fungicidal agents of the present invention are those wherein
X and Y are each independently hydrogen, halogen or $C_1$-$C_6$ alkyl;
m and n are each independently an integer of 0, 1 or 2;
A is O;
R, $R_1$, $R_2$ and $R_3$ are each independently hydrogen, halogen, $C_1$-$C_4$ alkyl, $C_1$-$C_4$ hydroxyalkyl, nitro, $NR_6R_7$ or $SO_3R_8$, and when taken together, R and $R_1$ or $R_1$ and $R_2$ may form a ring in which $RR_1$ or $R_1R_2$ is represented by the structure: —CH=CH—CH=CH—;
$R_4$ is hydrogen;
$R_5$ is hydrogen, $SO_3R_8$, oxo or phenyl, provided that when $R_5$ is oxo, $R_4$ is not present;
W is $(CH_2)_p$;
p is an integer of 0 or 1; and
$R_6$, $R_7$ and $R_8$ are each independently hydrogen or $C_1$-$C_4$ alkyl.

Other preferred compounds of the invention include those wherein
X and Y are each independently hydrogen, halogen, or $C_1$-$C_6$ alkyl;
m and n are each independently an integer of 0, 1, 2 or 3;
A is O or S;
R, $R_1$, $R_2$ and $R_3$ are each independently hydrogen, halogen, $C_1$-$C_4$ alkyl, $C_1$-$C_4$ hydroxyalkyl, nitro, $NR_6R_7$ or $SO_3R_8$, and when taken together, R and $R_1$ or $R_1$ and $R_2$ may form a ring in which $RR_1$ or $R_1R_2$ is represented by the structure: —CH=CH—CH=CH—;
$R_4$ is hydrogen, halogen, $C_1$-$C_8$ alkoxy or $C_1$-$C_8$ alkyl;
$R_5$ is hydrogen, halogen, $C_1$-$C_8$ alkoxy, $C_1$-$C_8$ alkyl, $NR_6R_7$, $SO_3R_8$, hydroxy, oxo or phenyl optionally substituted with one or more halogen, $C_1$-$C_4$ alkyl, $C_1$-$C_4$ haloalkyl, $C_1$-$C_4$ alkoxy or $C_1$-$C_4$ haloalkoxy groups, provided that when $R_5$ is oxo, $R_4$ is not present;
W is $(CH_2)_p$;
p is an integer of 0 or 1; and
$R_6$, $R_7$ and $R_8$ are each independently hydrogen or $C_1$-$C_4$ alkyl.

Especially preferred fungicidal compounds are those wherein
X and Y are each independently hydrogen or halogen;
m and n are each independently an integer of 0, 1 or 2;
A is O;
R, $R_1$, $R_2$ and $R_3$ are each independently hydrogen, $C_1$-$C_4$ alkyl, $C_1$-$C_4$ hydroxyalkyl, and when taken together R and $R_1$ may form a ring in which $RR_1$ is represented by the structure: —CH=CH—CH=CH—;
$R_4$ is hydrogen; and
$R_5$ is hydrogen.

Formula I diarylboron ester compounds which are particularly effective as fungicidal agents include
1,1-diphenyl-2-oxa-7a-azonia-1-borataindan; 2,3-dihydro-1,1-diphenyl-2-oxa-9b-azonia-1-borata-1H-benz[e]indene;
1,1-bis(p-chlorophenyl)-6-methyl-2-oxa-7a-azonia-1-borataindan; and
1,1-bis(p-chlorophenyl)-2-oxa-7a-azonia-1-borataindan, among others.

The term halogen used herein includes fluorine, chlorine, bromine and iodine. The term "medium" used herein is defined as any environment, including but not limited to artificial nutrients or soil, in which a plant can be kept, live or thrive.

The fungicidal diarylboron ester and thioester compounds of the present invention are particularly useful in the prevention, control or amelioration of diseases such as apple scab, tomato early blight and grape or pepper botrytis. Such diseases are caused by the phytopathogenic fungi *Venturia inaequalis*, *Alternaria solani* and *Botrytis cinerea*, respectively.

Fungicidal diarylboron ester and thioester compounds of formula I may be prepared by reacting a substituted pyridine of formula II with a diarylborinic acid of formula III as shown in Flow Diagram I.

FLOW DIAGRAM I

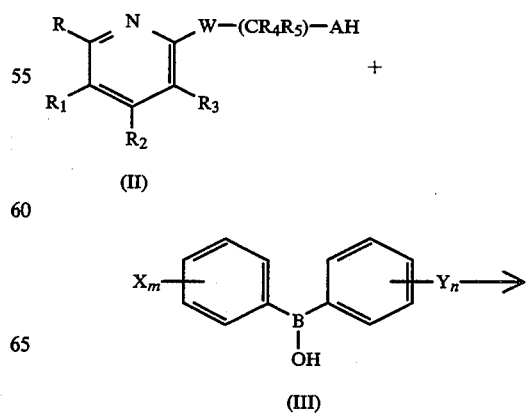

-continued
FLOW DIAGRAM I

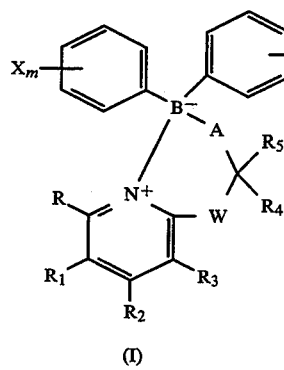

(I)

The formula I compounds are also useful for the protection of growing or harvested plants from the damage caused by photopathogenic fungal disease when applied to said plants at a fungicidally effective rate. The effective rate will vary depending upon factors such as the virulence of the target fungus, the environment of the treatment and other ambient conditions. In practice, generally about 20 ppm to about 1,000 ppm, preferably about 50 ppm to about 500 ppm of a formula I compound may be dispersed in a liquid or solid carrier and applied to the plant, seed or tuber, or to the medium or water in which the plant, seed or tuber is growing.

The fungicidal compounds of the invention may be formulated as concentrated solutions, emulsifiable concentrates, flowable concentrates, microemulsions and the like. Said compounds may also be formulated as dry compacted granules, granular compositions, dusts, dust concentrates, suspension concentrates, wettable powders, and the like. Those formulations which lend themselves to seed, tuber, medium, water and/or foliage applications to provide the requisite plant protection are suitable. Such formulations include the formula I compounds admixed with an inert solid or liquid carrier.

It is contemplated that the fungicidal compounds of the invention may be used in conjunction with, or in combination with, a pesticidally effective amount of one or more other pesticides, including but not limited to, anilazine, benalaxyl, benomyl, bitertanol, bordeaux mixture, carbendazim, carboxin, captafol, captan, chlorothalonil, cyproconazole, dichloran, diethofencarb, diniconazole, dithianon, dodine, edifenphos, fenarimol, fenbuconazole, fenfuram, fenpropidin, fenpropimorph, fentin hydroxide, ferbam, flusilazole, flusulfamide, flutriafol, folpet, fosetyl, fuberidazole, guazatine, hex-aconazole, imazalil, iprobenfos, iprodione, mancozeb, maneb, metalaxyl, metiram, myclobutanil, nuarimol, ofurace, oxadixyl, oxycarboxin, penconazole, probenazole, prochloraz, propiconazole, pyrazophos, tebuconazole, thiabendazole, thiophanate, thiophanate-methyl, triadimefon, triadimenol, triarimol, tricyclazole, tridemorph, triflumizole, triforine, vinclozolin, and/or zineb.

Where compositions of the invention are to be employed in combination treatments with other pesticidal agents, the composition may be applied concurrently as an admixture of the components as described above, or may be applied sequentially.

In order to facilitate a further understanding of the invention, the following examples are presented primarily for the purpose of illustrating more specific details thereof. The invention should not be deemed limited thereby except as defined in the claims.

EXAMPLE 1

Preparation of 1,1-Diphenyl-2-oxa-7a-azonia-1-borataindan

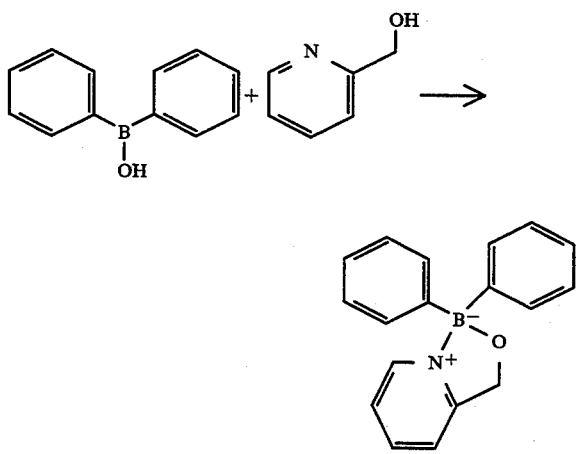

A mixture of diphenylborinic acid (1.0 g, 5.5 mmol) and 2-pyridinemethanol (0.53 mL, 5.5 mmol) in diethyl ether is refluxed overnight and filtered to obtain the title product as a white solid (1.4 g, mp 150°–152° C.).

Using essentially the same procedure, and employing the appropriately substituted diphenylborinic acid and 2-pyridinemethanol, 1-isoquinolinemethanol or 2-quinolinemethanol, the following compounds are obtained:

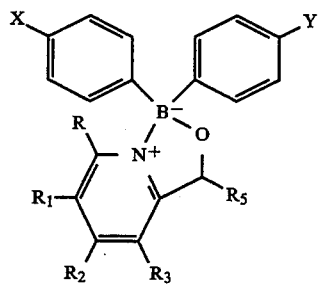

| X | Y | R | $R_1$ | $R_2$ | $R_3$ | $R_5$ | mp °C. |
|---|---|---|---|---|---|---|---|
| H | H | H | H | H | H | $SO_3H$ | 291–294 |
| F | F | H | H | H | H | H | 239–244 |
| H | H | H | H | —CH=CH—CH=CH— | | $C_6H_5$ | 225–226 |

-continued

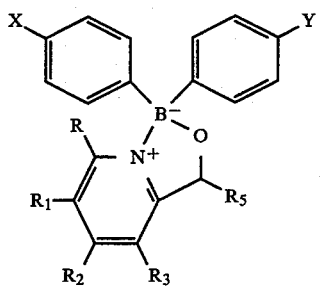

| X | Y | R | $R_1$ | $R_2$ | $R_3$ | $R_5$ | mp °C. |
|---|---|---|---|---|---|---|---|
| H | H | —CH=CH—CH=CH— | | H | H | $C_6H_5$ | 180–181 |
| H | H | —CH=CH—CH=CH— | | H | H | H | 175.5–176 |
| Cl | Cl | $CH_2OH$ | H | H | H | H | 88–90 |
| Cl | Cl | H | $CH_3$ | H | H | H | 135–143 |
| Cl | Cl | H | H | H | H | H | 133–134 |

EXAMPLE 2

Preparation of
2,3-Dihydro-1,1-diphenyl-2-oxa-9b-azonia-1-borata-1H-benz[e]indene-3-one

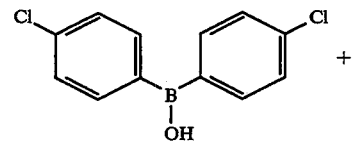

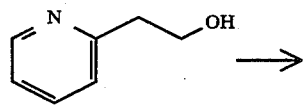

Diphenylborinic acid (0.77 g, 4.2 mmol) is added to a suspension of quinaldic acid (0.73 g, 4.2 mmol) in an ethanol/water (1:1) solution. The reaction mixture is stirred at room temperature for several days and filtered to give a solid. The solid is dried in a vacuum oven to obtain the title product as a white solid, mp 248°–249° C.

Using essentially the same procedure, but substituting 3-isoquinaldic acid for quinaldic acid, 1,1-diphenyl-2-oxa-9a-azonia-1-borata-1H-benz[f]inden-3(2H)-one is obtained an an off-white solid, mp 244.5°–245° C.

EXAMPLE 3

Preparation of
1,1-Bis(p-chlorophenyl)-1,2,3,4-tetrahydro-2-oxa-8a-azonia-1-boratanaphthalene

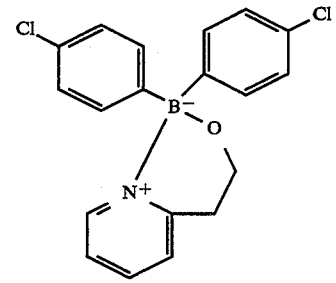

A mixture of [(bis-p-chloro)diphenyl]borinic acid (0.45 g, 1.5 mmol) and 2-hydroxyethylpyridine (0.18 g, 1.5 mmol) in diethyl ether is stirred at room temperature for 24 hours and filtered to obtain the title product as a white solid (0.22 g, mp 117°–119° C.).

EXAMPLE 4

Evaluation of in vivo fungicidal activity of test compounds

Test compounds are dissolved or suspended in acetone and diluted with deionized water containing about 0.05% TWEEN 20, a polyoxyethylene sorbitan monolaurate surfactant manufactured by Atlas Chemical Industries, to give a concentration of 200 ppm.

Host plants are sprayed with the test solution, dried and inoculated with fungi. When disease symptom development is optimal, the plants are rated for disease control according to the rating scale shown below.

Each test contains inoculated treated plants, inoculated untreated plants and a reference standard. When more than one test is run, the data are averaged. The data obtained are shown in Table I.

Compounds employed in this in vivo fungicidal evaluation and in the in vitro fungicidal evaluation in the following example are given a compound number and identified by name. Data in Table I are reported by compound number.

| RATING SCALE | |
|---|---|
| Rating | Range % Control |
| 0 | 0 |
| 1 | 1–14 |
| 2 | 15–29 |
| 3 | 30–44 |
| 4 | 45–59 |
| 5 | 60–74 |
| 6 | 75–89 |
| 7 | 90–95 |
| 8 | 96–99 |
| 9 | 100 |
| — | no evaluation |

| PHYTOPATHOGENIC FUNGI | | |
|---|---|---|
| Symbol | Disease | Pathogen |
| AS | Apple Scab | *Venturia inaequalis* |
| GDM | Grape Downy Mildew | *Plasmopara viticola* |
| PB | Pepper Botrytis | *Botrytis cinerea* |
| RB | Rice Blast | *Pyricularia oryzae* |
| SBC | Sugar Beet Cercospora | *Cercospora beticola* |
| TEB | Tomato Early Blight | *Alternaria solani* |
| WPM | Wheat Powdery Mildew | *Erysiphe graminis f. sp. tritici* |
| WSN | Wheat Septoria Nodorum Blotch | *Septoria nodorum* |

| COMPOUNDS EVALUATED AS FUNGICIDAL AGENTS | |
|---|---|
| Compound No. | |
| 1 | 1,1-Diphenyl-2-oxa-7a-azonia-1-borataindan |
| 2 | 1,1-Diphenyl-2-oxa-7a-azonia-1-borataindan-3-sulfonic acid |
| 3 | 1,1-Bis(p-fluorophenyl)-2-oxa-7a-azonia-1-borataindan |
| 4 | 2,3-Dihydro-1,1-diphenyl-2-oxa-9b-azonia-1-borata-1H-benz[e]indene |
| 5 | 1,1-Diphenyl-2-oxa-9a-azonia-1-borata-1H-benz[f]inden-3(2H)-one |
| 6 | 2,3-Dihydro-1,1,3-triphenyl-2-oxa-9a-azonia-1-borata-1H-benz[f]indene |
| 7 | 2,3-Dihydro-1,1,3-triphenyl-2-oxa-9b-azonia-1-borata-1H-benz[e]indene |
| 8 | 1,1-Bis(p-chlorophenyl)-1,2,3,4-tetrahydro-2-oxa-8a-azonia-1-boratanaphthalene |
| 9 | 1,1-Bis(p-chloro-phenyl)-2-oxa-7a-azonia-1-borataindan |
| 10 | 1,1-Bis(p-chlorophenyl)-6-methyl-2-oxa-7a-azonia-1-borataindan |
| 11 | 2,3-Dihydro-1,1-diphenyl-2-oxa-9b-azonia-1-borata-1H-benz[e]indene-3-one |
| 12 | 1,1-(p-Chlorophenyl)-7-(hydroxymethyl)-2-oxa-7a-azonia-1-borataindan |

TABLE I

| | | In Vivo Fungicidal Evaluations | | | | | | | |
|---|---|---|---|---|---|---|---|---|---|
| Compound Number | Rate (ppm) | AS | GDM | PB | RB | SBC | TEB | WPM | WSN |
| 1 | 200 | 9 | 8 | 9 | 0 | 5 | 6 | 0 | — |
| 2 | 200 | 0 | 0 | 0 | 0 | 0 | 0 | 2 | 0 |
| 3 | 200 | 6 | 4 | 0 | 0 | 8 | 8 | 6 | 0 |
| 4 | 200 | 6 | 2 | 9 | 6 | 0 | 6 | 0 | 0 |
| 5 | 200 | 0 | 0 | 6 | 0 | 0 | 0 | 0 | 0 |
| 6 | 200 | 4 | 0 | 0 | 0 | 0 | 0 | 0 | 0 |
| 7 | 200 | 0 | 0 | 0 | 0 | 0 | 0 | 0 | 0 |
| 8 | 200 | 6 | 7 | 0 | 0 | 0 | 0 | 6 | 0 |
| 9 | 200 | 6 | 6 | 5 | 0 | 5 | 3 | 0 | 0 |
| 10 | 200 | 8 | 7 | 7 | 0 | 0 | 0 | 0 | 0 |
| 11 | 200 | 0 | 0 | 0 | 0 | 0 | 0 | 0 | 0 |
| 12 | 200 | 4 | 4 | 7 | 4 | 0 | 2 | 0 | 4 |

EXAMPLE 5

Evaluation of in vitro fungicidal activity of test compounds

Test compounds are dissolved or suspended in acetone and dispersed into cell well plates containing a suspension of ground fungal mycelia in a nutrient broth. Assay plates are incubated for 3–4 days at 21° C. Growth inhibition is measured visually and is rated using the following scale:

| Rating | % Inhibition |
|---|---|
| 0 | 0 |
| 1 | 1–29 |
| 3 | 30–59 |
| 5 | 60–89 |
| 7 | 90–99 |
| 9 | 100 |

Untreated controls, solvent blanks and reference standards are included in each test.

Assay fungi include the plant pathogens, *Pythium ultimum* (Pythul); *Rhizoctonia solani* (Rhizso); *Fusarium oxysporum* f. sp. cucumerinum (Fusoxc); and *Pseudocercosporella herpotrichoides* (Psdche).

When more than one test is run, the data are averaged. The data obtained are shown in Table II. The compounds evaluated are reported by compound number given in Example 4.

TABLE II

| | | In Vitro Fungicidal Evaluations | | | |
|---|---|---|---|---|---|
| Compound Number | Rate (ppm) | FUSOXC | PSDCHE | PYTHUL | RHIZSO |
| 1 | 25 | 9 | 5 | 9 | 9 |
| 2 | 25 | 7 | 5 | 7 | 9 |
| 3 | 25 | 7 | 5 | 7 | 9 |

TABLE II-continued

In Vitro Fungicidal Evaluations

| Compound Number | Rate (ppm) | FUSOXC | PSDCHE | PYTHUL | RHIZSO |
|---|---|---|---|---|---|
| 4 | 25 | 9 | 9 | 9 | 9 |
| 5 | 25 | 3 | 5 | 5 | 0 |
| 6 | 25 | 0 | 0 | 0 | 0 |
| 7 | 25 | 3 | 0 | 3 | 0 |
| 8 | 25 | 9 | 9 | 9 | 9 |
| 9 | 25 | 7 | 9 | 9 | 7 |
| 10 | 25 | 5 | 9 | 9 | 7 |
| 11 | 25 | 5 | 0 | 7 | 5 |
| 12 | 25 | 7 | 9 | 9 | 5 |

I claim:

1. A method for the prevention, control or amelioration of a disease caused by a phytopathogenic fungus which comprises contacting said fungus with a fungicidally effective amount of a compound having the structural formula

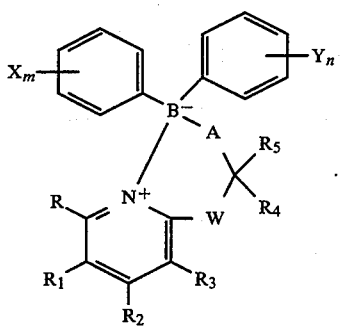

wherein
X and Y are each independently hydrogen, halogen, or $C_1$-$C_6$ alkyl;
m and n are each independently an integer of 0, 1, 2 or 3;
A is O or S;
R, $R_1$, $R_2$ and $R_3$ are each independently hydrogen, halogen, $C_1$-$C_4$ alkyl, $C_1$-$C_4$ hydroxyalkyl, nitro, $NR_6R_7$ or $SO_3R_8$, and when taken together, R and $R_1$ or $R_1$ and $R_2$ may form a ring in which $RR_1$ or $R_1R_2$ is represented by the structure: —CH=CH—CH=CH—;
$R_4$ is hydrogen, halogen, $C_1$-$C_8$ alkoxy or $C_1$-$C_8$ alkyl;
$R_5$ is hydrogen, halogen, $C_1$-$C_8$ alkoxy, $C_1$-$C_8$ alkyl, $NR_6R_7$, $SO_3R_8$, hydroxy, oxo or phenyl optionally substituted with one or more halogen, $C_1$-$C_4$ alkyl, $C_1$-$C_4$ haloalkyl, $C_1$-$C_4$ alkoxy or $C_1$-$C_4$ haloalkoxy groups, provided that when $R_5$ is oxo, $R_4$ is not present;
W is $(CH_2)_p$;
p is an integer of 0 or 1; and
$R_6$, $R_7$ and $R_8$ are each independently hydrogen or $C_1$-$C_4$ alkyl.

2. The method according to claim 1 wherein
X and Y are each independently hydrogen or halogen;
m and n are each independently an integer of 0, 1 or 2;
A is O;
R, $R_1$, $R_2$ and $R_3$ are each independently hydrogen, $C_1$-$C_4$ alkyl, $C_1$-$C_4$ hydroxyalkyl, and when taken together R and $R_1$ may form a ring in which $RR_1$ is represented by the structure: —CH=CH—CH=CH—;
$R_4$ is hydrogen; and
$R_5$ is hydrogen.

3. The method according to claim 2 wherein the compound is selected from the group consisting of
1,1-diphenyl-2-oxa-7a-azonia-1-borataindan;
2,3-dihydro-1,1-diphenyl-2-oxa-9b-azonia-1-borata-1H-benzindene;
1,1-bis(p-chlorophenyl)-6-methyl-2-oxa-7a-azonia-1-borataindan; and
1,1-bis(p-chlorophenyl)-2-oxa-7a-azonia-1-borataindan.

4. The method according to claim 1 wherein the compound is applied at a concentration of about 20 ppm to 1,000 ppm.

5. A method for the protection of a plant, plant seed or tuber from fungal infestation and disease which comprises applying to the plant, plant seed or tuber, or to the soil or water in which it is growing a fungicidally effective amount of a compound having the structural formula

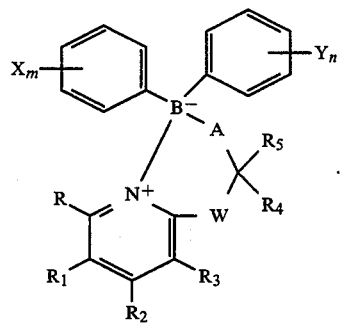

wherein
X and Y are each independently hydrogen, halogen, or $C_1$-$C_6$ alkyl;
m and n are each independently an integer of 0, 1, 2 or 3;
A is O or S;
R, $R_1$, $R_2$ and $R_3$ are each independently hydrogen, halogen, $C_1$-$C_4$ alkyl, $C_1$-$C_4$ hydroxyalkyl, nitro, $NR_6R_7$ or $SO_3R_8$, and when taken together, R and $R_1$ or $R_1$ and $R_2$ may form a ring in which $RR_1$ or $R_1R_2$ is represented by the structure: —CH=CH—CH=CH—;
$R_4$ is hydrogen, halogen, $C_1$-$C_8$ alkoxy or $C_1$-$C_8$ alkyl;
$R_5$ is hydrogen, halogen, $C_1$-$C_8$ alkoxy, $C_1$-$C_8$ alkyl, $NR_6R_7$, $SO_3R_8$, hydroxy, oxo or phenyl optionally substituted with one or more halogen, $C_1$-$C_4$ alkyl, $C_1$-$C_4$ haloalkyl, $C_1$-$C_4$ alkoxy or $C_1$-$C_4$ haloalkoxy groups, provided that when $R_5$ is oxo, $R_4$ is not present;
W is $(CH_2)_p$;
p is an integer of 0 or 1; and
$R_6$, $R_7$ and $R_8$ are each independently hydrogen or $C_1$-$C_4$ alkyl.

6. The method according to claim 5 wherein
X and Y are each independently hydrogen or halogen;
m and n are each independently an integer of 0, 1 or 2;
A is O;
R, $R_1$, $R_2$ and $R_3$ are each independently hydrogen, $C_1$-$C_4$ alkyl, $C_1$-$C_4$ hydroxyalkyl, and when taken together R and R₁ may form a ring in which RR₁ is represented by the structure: —CH=CH—CH=CH—;
R₄ is hydrogen; and
R₅ is hydrogen.

7. The method according to claim 6 wherein the compound is selected from the group consisting of 1,1-diphenyl-2-oxa-7a-azonia-1-borataindan;
2,3-dihydro-1,1-diphenyl-2-oxa-9b-azonia-1-borata-1H-benzindene;
1,1-bis(p-chlorophenyl)-6-methyl-2-oxa-7a-azonia-1-borataindan; and
1,1-bis(p-chlorophenyl)-2-oxa-7a-azonia-1-borataindan.

\* \* \* \* \*